US010539682B2

(12) United States Patent
Jacobs et al.

(10) Patent No.: US 10,539,682 B2
(45) Date of Patent: Jan. 21, 2020

(54) MEDICAL IMAGING DETECTOR

(71) Applicant: KONINKLIJKE PHILIPS N.V., Eindhoven (NL)

(72) Inventors: Johannes Wilhelmus Maria Jacobs, Eindhoven (NL); Walter Ruetten, Eindhoven (NL); Matthias Simon, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 194 days.

(21) Appl. No.: 15/550,418

(22) PCT Filed: Feb. 3, 2016

(86) PCT No.: PCT/EP2016/052211
§ 371 (c)(1),
(2) Date: Aug. 11, 2017

(87) PCT Pub. No.: WO2016/131647
PCT Pub. Date: Aug. 25, 2016

(65) Prior Publication Data
US 2018/0024253 A1 Jan. 25, 2018

(30) Foreign Application Priority Data
Feb. 17, 2015 (EP) .................................... 15155322

(51) Int. Cl.
*G01T 1/16* (2006.01)
*A61B 6/00* (2006.01)
(Continued)

(52) U.S. Cl.
CPC .......... *G01T 1/1603* (2013.01); *A61B 6/4417* (2013.01); *A61B 5/0024* (2013.01);
(Continued)

(58) Field of Classification Search
CPC ..... G01T 1/1603; A61B 6/4417; A61B 6/563; A61B 5/0024; A61B 5/0035;
(Continued)

(56) References Cited

U.S. PATENT DOCUMENTS 5,548,123 A 8/1996 Perez-Mendez
5,983,123 A 11/1999 Shmulewitz
(Continued)

FOREIGN PATENT DOCUMENTS

DE 102012210076 A1 12/2013
EP 1304070 A2 4/2003
(Continued)

*Primary Examiner* — David P Porta
*Assistant Examiner* — Jeremy S Valentiner
(74) *Attorney, Agent, or Firm* — Larry Liberchuk

(57) ABSTRACT

The present invention relates to medical imaging, and in particular a medical imaging detector. In order to improve and facilitate the collection of information, e.g. for medical diagnosis, a medical imaging detector is provided that comprises a first sensor arrangement (12) and a second sensor arrangement (14). The first sensor arrangement is configured to provide a first type of image data belonging to a first imaging modality. The second sensor arrangement is configured to provide a second type of image data belonging to a second imaging modality. The first imaging modality is an X-ray imaging modality, while the second imaging modality is a non-X-ray imaging modality. The first sensor arrangement comprises one or a plurality of first sensor segments (16) arranged within a first circumferential line (18) defining a first imaging area (20). The second sensor arrangement comprises one or a plurality of second sensor segments (22) arranged within a second circumferential line (24) defining a second imaging area (26). The first imaging area and the second imaging area at least partly overlap.

12 Claims, 4 Drawing Sheets

(51) Int. Cl.
  *A61B 5/00* (2006.01)
  *A61B 8/00* (2006.01)
(52) U.S. Cl.
  CPC ........... *A61B 5/0035* (2013.01); *A61B 5/0075* (2013.01); *A61B 5/0077* (2013.01); *A61B 6/563* (2013.01); *A61B 8/4416* (2013.01); *A61B 2562/0204* (2013.01); *A61B 2562/0219* (2013.01); *A61B 2562/0223* (2013.01); *A61B 2562/12* (2013.01)
(58) Field of Classification Search
  CPC ....... A61B 5/0075; A61B 5/0077; A61B 5/65; A61B 8/4416; A61B 2562/0204; A61B 2562/0219; A61B 2562/0223; A61B 2562/12
  See application file for complete search history.

(56) References Cited

U.S. PATENT DOCUMENTS

| | | |
|---|---|---|
| 6,448,559 B1 | 9/2002 | Saoudi |
| 7,864,917 B2 | 1/2011 | Ribbing |
| 9,597,046 B2 | 3/2017 | Goossen |
| 2002/0090050 A1 | 7/2002 | Nutt |
| 2003/0082104 A1 | 5/2003 | Mertelmeier |
| 2003/0128801 A1 | 7/2003 | Eisenberg |
| 2003/0187349 A1 | 10/2003 | Kaneko |
| 2004/0249271 A1* | 12/2004 | Besson ............... A61B 6/488 600/427 |
| 2006/0124832 A1* | 6/2006 | Harmon ............... G01T 1/24 250/214 R |
| 2007/0176109 A1* | 8/2007 | Bell ............... G01T 1/2018 250/370.09 |
| 2008/0242979 A1* | 10/2008 | Fisher ............... A61B 6/4233 600/427 |
| 2010/0111250 A1* | 5/2010 | Tsujii ............... A61B 5/0091 378/37 |
| 2011/0089327 A1* | 4/2011 | Vija ............... A61B 6/4241 250/363.04 |
| 2013/0027040 A1 | 1/2013 | Alagappan |
| 2013/0053679 A1 | 2/2013 | Owen |

FOREIGN PATENT DOCUMENTS

| | | |
|---|---|---|
| WO | 2004042546 A1 | 5/2004 |
| WO | 2013190434 A1 | 12/2013 |
| WO | 2014139018 A1 | 9/2014 |

* cited by examiner

MEDICAL IMAGING DETECTOR

CROSS-REFERENCE TO PRIOR APPLICATIONS

This application is the U.S. National Phase application under 35 U.S.C. § 371 of International Application No. PCT/EP2016/052211, filed on Feb. 3, 2016, which claims the benefit of European Patent Application No. 15155322.9, filed on Feb. 17, 2015. These applications are hereby incorporated by reference herein.

FIELD OF THE INVENTION

The present invention relates to a medical imaging detector, to a medical imaging system, and to a medical imaging method, as well as to a computer program element and to a computer readable medium.

BACKGROUND OF THE INVENTION

Medical imaging is used to obtain anatomical information of an object of interest, e.g. a portion of a patient. For example, X-rays can be used for recording images of the internal structure of the body to assess the presence or absence of disease, foreign objects, and structural damage or anomaly. WO 2013/190434 A1 describes a radiation detector with organic photodiodes. However, it has been shown that X-ray imaging is not always suitable for providing particular types of patient related information. For example, the information about blood flow may not be provided by X-ray images unless specific contrast agents are injected.

US2013/027040A1 describes a magnetic resonance radiofrequency coil formed from carbon nanotube conductors transparent to e.g. X-ray radiation.

US2011/089327A1 describes an imaging system including interleaved emission detectors and transmission detectors.

US2003/128801A1 describes a multi-modality imaging system that can be utilized in volume computed tomography (VCT) mode, single photon emission computed tomography (SPECT) mode and positron emission tomography (PET) mode.

SUMMARY OF THE INVENTION

There may be a need to provide a medical imaging detector with improved and facilitated collection of information, e.g. for medical diagnosis.

The object of the present invention is solved by the subject-matter of the independent claims, wherein further embodiments are incorporated in the dependent claims. It should be noted that the following described aspects of the invention apply also for the medical imaging detector, for the medical imaging system, for the medical imaging method, for the computer program element and for the computer readable medium.

According to a first aspect of the present invention, a medical imaging detector is provided that comprises a first sensor arrangement, a second sensor arrangement and at least one substrate structure. The first sensor arrangement is configured to provide a first type of image data belonging to a first imaging modality. The second sensor arrangement is configured to provide a second type of image data belonging to a second imaging modality. The first imaging modality is an X-ray imaging modality, while the second imaging modality is a non-X-ray imaging modality. The first sensor arrangement comprises one or a plurality of first sensor segments arranged within a first circumferential line defining a first imaging area. The second sensor arrangement comprises one or a plurality of second sensor segments arranged within a second circumferential line defining a second imaging area. The first imaging area and the second imaging area at least partly overlap. The one or a plurality of first sensor segments and the one or a plurality of second sensor segments are arranged on the at least one substrate structure As an advantage, combining two or more imaging sensors with a partly overlapping imaging area for different types of radiation or information provides a user, e.g. a doctor, with more complete information about anatomy and function of a patient. For example, X-ray images provide detailed anatomical information, but do not provide any information about blood flow unless specific contrast agents are injected. On the other hand, ultrasound can deliver accurate information about blood velocity and blood flow, but may lack anatomical detail and penetration depth compared to X-ray. As another example, hyper-spectral cameras can deliver additional information about the skin, e.g. information from upper layers of tissues, which information is not available with either X-ray or ultrasound images. The combination of an X-ray sensor, an ultrasound probe and a hyper-spectral camera can thus enable a medical doctor not only to obtain detailed anatomical information, but also to obtain the information about blood flow and blood velocity and the information from upper layers of tissues. This allows simultaneous measurement or acquisition of different images in the same patient location, thus providing consistent augmented information about the patient for a better diagnosis and treatment of medical conditions. Although the different sensors could be used in a sequential way on different systems, this may lead to increased errors since the patient's state and posture can change between different examinations. Further, simultaneous use of those different sensors may be hindered by space constraints that may arise from using individual sensor with their housing, cabling and infrastructure.

According to the invention, the medical imaging detector comprises at least one substrate structure. The one or a plurality of first sensor segments and the one or a plurality of second sensor segments are arranged on the at least one substrate structure.

The integration of different sensors on a single substrate, or substrate structure, enables a compact design. For example, different types of sensors can be built on the substrate based on the same base technology of semiconductor processing, e.g. complementary metal-oxide-semiconductor (CMOS) and microelectromechanical systems (MEMS) processes. The sensors can also be built on the substrate based on different base technology, e.g. sensors fabricated on foil can be integrated with CMOS sensors by lamination or gluing.

According to an example, the second sensor segment is a light sensor provided as at least one of the group of: a visible light sensor, an ultraviolet light sensor, an infrared light sensor, and a hyper-spectral sensor.

Optical imaging, such as hyper-spectral imaging, can provide diagnostic information about the tissue physiology, morphology, and composition.

According to an example, the second sensor segment is an acoustic sensor provided as at least one of the group of: an audible sound sensor, an ultrasound sensor, and an infrasound sensor.

The acoustic sensors, such as ultrasound sensors, provide additional clinically relevant information to the primary X-ray image, e.g. image content like soft tissues and blood flow. The sensor can comprise sound transmitters or have shared transmitters and receivers, so called transducers.

It is noted that the term "acoustic sensor" also relates to acoustic transceivers or transducers having both transmit and receive functions.

According to an example, the second sensor segment is a radiation sensor provided as at least one of the group of: a terahertz radiation sensor, and a gigahertz radiation sensor.

The terahertz or gigahertz radiation sensors may be used to detect differences in water content and density of a tissue.

The term "radiation sensor" also relates to radiation transceivers or transducers to transmit and receive terahertz/gigahertz radiation, e.g. small aerials tuned to the desired transmission/reception frequency.

According to an example, the medical imaging detector further comprises a third sensor arrangement. The third sensor arrangement comprises one or a plurality of third sensor segments arranged on the at least one substrate structure. The third sensor segment(s) is (are) a non-imaging sensor(s) provided as at least one of the group of: a telemetry transceivers, a body area network transceiver, an electric field sensor, a magnetic field sensor, an attitude sensor, an acceleration sensor, a motion sensor, and a rotation sensor.

By providing the non-imaging sensors, the information about electric fields, magnetic fields, attitude, motion or acceleration of an object, or about rotation of an object or the detector can be obtained. As an advantage, the X-ray image acquisition can be optimized by sensing patient movements. In addition, X-ray settings can be improved, e.g. by measurement of patient thickness and the distance between the X-ray source and the patient.

According to an example, the second sensor arrangement is arranged on the outer periphery of the first imaging area.

The term "periphery" refers to the outer edge of the first imaging area, i.e. the area surrounding the first imaging area.

According to an example, the first sensor segments and the second sensor segments are interleaved in a common imaging area.

According to an example, in a dual-imaging area, at least a part of the first sensor segments and the second sensor segments are arranged overlapping to provide dual imaging information for a common imaging area.

According to an example, the first sensor arrangement and the second sensor arrangement are arranged on opposite sides of the at least one substrate structure.

According to a second aspect of the present invention, a medical imaging system is provided that comprises a medical imaging detector according to one of the above-mentioned examples and a first imaging source. The first imaging source is an X-ray source configured to provide X-ray radiation as a first type of radiation to be detected by the first sensor arrangement of the medical imaging detector.

According to an example, the medical imaging system further comprises a second imaging source. The second imaging source is configured to provide a signal to be detected by the second sensor arrangement of the medical imaging detector. The second imaging source is provided as at least one of the group of: a light source, an acoustic source, and a radiation source.

According to a third aspect of the present invention, a medical imaging method is provided, the method comprising the following:

a) performing a first imaging modality examination and a second imaging modality examination on an object; and b) obtaining first image data of the first imaging modality and the second image data of the second imaging modality with a medical imaging detector.

The first imaging modality is an X-ray imaging modality, while the second imaging modality is a non-X-ray imaging modality. The first image data is acquired in a first imaging area and the second image data is acquired in a second imaging area. The first imaging area and the second imaging area at least partly overlap. One or a plurality of first sensor segments and one or a plurality of second sensor segments are arranged on at least one substrate structure.

According to an aspect of the present invention, a medical imaging detector is provided that comprises two or more sensors for different types of radiation or information including, for example, X-ray sensors, acoustic sensors, optical sensors/cameras, terahertz and gigahertz sensors, and also non-imaging sensors, such as motion sensors. Such combinations will allow simultaneous measurement or acquisition of different types of image data in the same patient location and thus provide consistent augmented information about the patient. The different types of sensors can be built on the same substrate, e.g. a crystalline silicon (c-Si) wafer, a glass plate, a ceramic plate or a foil. Mixed approaches, e.g. a CMOS sensors placed next to an amorphous silicon (a-Si:H) sensor combine the strengths of both technologies. Also sensors-on-foil lend themselves for easy integration with other sensors by lamination or gluing. Manufacturing of two or more sensors on the same substrate is advantageous and is facilitated by use of the same base technology of semiconductor processing, especially by the widespread CMOS and MEMS processes.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
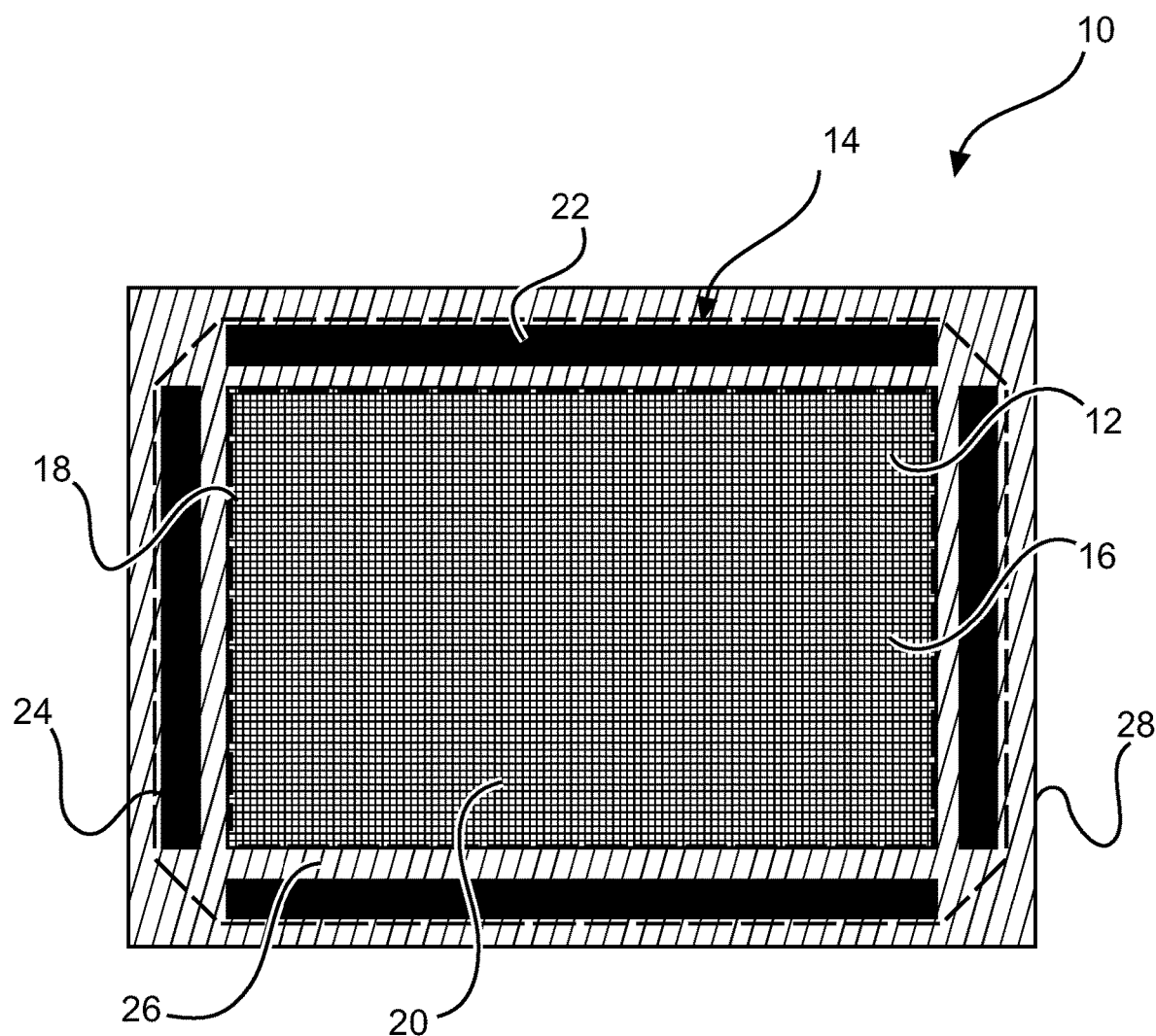
FIG. 1 shows an exemplary embodiment of a medical imaging detector in a schematic illustration.

FIG. 1 shows a schematic view of an example of a medical imaging detector 10. The medical imaging detector 10 comprises a first sensor arrangement 12 and a second sensor arrangement 14. The first sensor arrangement 12 is configured to provide a first type of image data belonging to a first imaging modality. The second sensor arrangement 14 is configured to provide a second type of image data belonging to a second imaging modality. The first imaging modality is an X-ray imaging modality, while the second imaging modality is a non-X-ray imaging modality.

The first sensor arrangement 12 comprises one or a plurality of first sensor segments 16 arranged within a first circumferential line 18, indicated with a dashed line, defining a first imaging area 20. As an example, the first sensor arrangement 12 in FIG. 1 comprises one first sensor segment 16 in form of a matrix of an X-ray sensor, which may use either indirect conversion or direct conversion pixels occupying the central part of the medical imaging detector 10. The first circumferential line 18 is the outline of the first sensor segment 16.

The second sensor arrangement 14 comprises one or a plurality of second sensor segments 22 arranged within a second circumferential line 24, indicated with another dashed line, defining a second imaging area 26. The first imaging area 20 the second imaging area 26 are at least partly overlap. As an example, the second sensor arrangement 14 in FIG. 1 comprises four second sensor segments 22, which are arranged on the outer periphery of the first imaging area 20. The second circumferential line 24 encloses the four second sensor segments 22. The second imaging area 26 is the area within the second circumferential line 24 and thus includes the first imaging area 20.

In a further example, the medical imaging detector 10 further comprises at least one substrate structure 28. The one or the plurality of first sensor segments 16 and the one or the plurality of second sensor segments 22 are arranged on the at least one substrate structure 28. As an example, the first sensor segment 16 and the four second sensor segments 22 in FIG. 1 are arranged on the same surface of the substrate structure 28.

The "medical imaging detector", which is also referred to as dual- or multi-modality medical imaging detector, relates to an imaging detector to acquire two or more different types of imaging data, which belong to different imaging modalities.

The "image data" relates to one- or multi-dimensional data composed of discrete image elements including, for example, pixels for 2D images or voxels for 3D images. The image may be, for example, a medical image of a subject collected by X-ray, computer tomography, ultrasound, terahertz imaging, or a hyper-spectral camera, etc. The "imaging modality" relates to various types of equipment or probes used to acquire images of the body, such as radiography and ultrasound.

The imaging modalities may be distinguished base on their wavelength, energy, and their interaction with an object, e.g. a portion of a patient. For example, X-rays can traverse the body. Light has a limited penetration depth. Terahertz/gigahertz radiation has also limited penetration depth. Depending on the wavelength, it is possible to probe different properties of the matter, e.g. specific absorption by different chemical compounds.

An X-ray imaging modality comprises single-, dual- and multiple-energy X-ray imaging.

A non-X-ray imaging modality may include ultrasound, optical, IR (infrared), UV (ultraviolet), hyper-spectral imaging or any other imaging modalities known to one of skill in the art.

The term "circumferential line" refers to a line that includes, encloses, or surrounds one or a plurality of sensor segments. In other words, the circumferential line serves as a boundary surrounding and linking sensor segments together. When there is only one sensor segment, the circumferential line refers to the outline of the sensor segment. When there are two or more sensor segments, the circumferential line refers to the outline of the sensor segments and the spaces in-between. The circumferential line may have different shapes, depending on the arrangement of the sensor segments. The circumferential line may have a convex form.

In another example, the circumferential line defines a minimum surface area enclosing all sensor segments. In a further example, as shown in FIG. 1, the circumferential line is the line enclosing all sensor segments, but with a minimum length.

In an example, the circumferential line has a circular, oval or elliptic shape. In another example, the circumferential line has a square or rectangular shape.

The "imaging area" refers to the area that is used for image acquisition purposes, i.e. for example, for acquiring X-ray images or ultrasound images or optical (camera) images. The imaging area comprises image segments (or parts or portions, or pixels) with image information and also image segments (or parts or portions, or pixels) without image information, so-to-speak blind or "silent" spots. However, even though in some parts image information is not acquired, it is possible to achieve at least a certain degree of information over the complete imaging area. For example, image information is acquired only for half of the imaging area, but distributed mainly around the outer portions, and hence the contour of the object or patient can be determined. For example, missing image content for the imaging area is added by interpolation. In an example, the interpolated parts are indicated as such to be different from the acquired image content. For ultrasound transducers and terahertz/gigahertz radiation, it is also possible to steer the transmit beams and receive beams electronically, e.g. by adjusting the phases between individual transducers or antennas. For UV/visible/IR imagers, lenses can be applied to adapt the viewing direction to the needs of the imaging task.

Although for some types of sensors, the "imaging area" is not equivalent to "object area". For example, a camera can image a full large object, i.e. a portion of a patient, with a small imaging area, i.e. pixel area or, in other words, the surface area of the sensor segments. Another example is an ultrasound sensor, which has a small imaging area compared to an imaged object area (or volume). It is noted that the "imaging area" in the context of the present invention relates not only to the surface areas of these sensor segments but also to the spaces in-between. For example, the second imaging area 26 comprises not only surface areas of the four second sensor segments 22 but also other surface areas inside the second circumferential line 24.

The "sensor segment" may be formed by a plurality of sensor part-segments, e.g. two part-segments tiled together. Each sensor segment or part-segment may be provided as a matrix of sensing elements, i.e. pixels, such as X-ray sensitive elements or light sensitive photodiodes with attached pixel electronics.

The "X-ray sensor" may comprise a matrix of X-ray sensitive elements, which may either use a direct technique (direct-conversion detectors) or an indirect technique (indirect-conversion detectors) for converting X-rays into an electric charge. Direct-conversion detectors have an X-ray photoconductor, such as amorphous selenium, that directly converts X-ray photons into an electric charge. Indirect-conversion detectors, on the other hand, have a scintillator that first converts X-rays into visible light. That light is then converted into an electric charge by means of photodetectors such as amorphous silicon photodiode arrays, CMOS imagers or CCDs. Thin-film transistor (TFT) arrays may be used in both direct- and indirect-conversion detectors.

The X-ray sensor may be made based on amorphous silicon (a-Si) TFT, low temperature recrystallized polycrystalline silicon (LTPS), organic transistors (OTFT) or amorphous oxide transistors (AOS) switch matrices. The X-ray sensor may be arranged on different types of substrates including, for example, glass, plastic foil, silicon, and ceramic substrate.

The X-ray sensor may also be a dual- or multilayer X-ray sensor for simultaneously acquiring two or more X-ray energy spectra during an X-ray exposure.

The "substrate structure" refers to a structure that comprises one or a plurality of substrates. The plurality of substrates may be, e.g. tiled together to form a larger substrate area. In another example, the plurality substrates may be stacked on top of each other to support different types of sensors, e.g. a glass substrate for X-ray sensors and a silicon substrate for CMOS image sensors.

"Tiling" refers to arranging several sub-substrates together but without covering each other. In this way, a larger detector is formed. For example, a plurality of sub-substrates can be attached to a supporting substrate to form one contiguous sensor. In an example, sub-substrates form part-segments.

The term "arranged on" the at least one substrate is also referred to as holding or fixedly supporting the segments by the substrate. The segments are attached to the substrate.

Arranging the first sensor segments and the second sensor segments on the at least one substrate structure may include deposition and lithography steps. Alternatively, the first and second sensor arrangements may be fabricated separately and then attached to the at least one substrate, e.g. by lamination or gluing of plastic foil substrates. The choice of the arrangement depends on various factors, such as the availability of manufacturing technologies for a certain substrate.

It will be appreciated that two different types of sensors may be arranged on the same substrate. Manufacturing of two or more sensors on the same substrate is advantageous and is facilitated by the use of the same base technology of semiconductor processing, e.g. by the CMOS and MEMS processes. For example, an X-ray sensor and a hyper-spectral sensor, or camera, are both fabricated in a CMOS process. Alternatively, different types of sensors may be manufactured on different types of substrates, and the substrates are attached to each other subsequently. As an example, an X-ray detector may be made using amorphous silicon thin-film technology on glass, also called a-Si thin film technology on glass, while hyper-spectral cameras may be fabricated in a CMOS process. The hyper-spectral cameras can thus be attached to the X-ray detector to form a unitary multifunctional imaging sensor.

Depending on the non-X-ray imaging modality that is required, the second sensor segment 22 may be a light sensor that comprises at least one of the group of: a visible light sensor, an ultraviolet light sensor, an infrared light sensor, and a hyper-spectra sensor.

The provision of an X-ray sensor and one or more optical, UV, IR and/or hyper-spectral sensors on the same substrate enables simultaneous X-ray and optical, UV, IR, and/or hyper-spectral imaging of the same patient area.

The visible light sensor may be a CMOS image sensor, which uses a matrix of light sensitive photodiodes with attached pixel electronics to provide images in the visible range of light. The wavelength ranges of the sensors can be extended into the UV range with special manufacturing steps.

The IR sensor may also be based on CMOS chips comprising photoconductors for the actual detection of infrared light. The photoconductors may be germanium (Ge), galliumarsenide (GaAs), indiumgalliumarsenide (InGaAs) and similar III-V or II-VI semiconductors.

The hyper-spectral sensor combines one or more of these wavelength ranges and provides a multitude images at different wavelengths.

It will be appreciated that the photodiodes can be made by any suitable manufacturing process. For example, the photodiodes for the visible, UV or IR range may be made using organic semiconductors on a plastic foil substrate.

In a further example, the second sensor segment 22 is an acoustic sensor that comprises at least one of the group of: an audible sound sensor, an ultrasound sensor, and an infrasound sensor.

The addition of acoustic sensors, e.g. one or more ultrasound transducer arrays, to the X-ray sensor enables simultaneous X-ray and ultrasound imaging, thus providing additional information like blood velocity and blood flow in arteries and veins.

The acoustic sensor may be conventional audible sound, ultrasound, or infrasound transducers that are suitable for reception and transmission of acoustic radiation. The sensors may also be MEMS sensors, such as capacitive micromachined ultrasonic transducers (CMUT) integrated with CMOS driver and amplifier arrays to form steerable ultrasound scanners.

In a still further example, the second sensor segment 22 is a radiation sensor that comprises at least one of the group of: a terahertz radiation sensor and a gigahertz radiation sensor.

Detection and transmission of terahertz (THz) and gigahertz (GHz) electromagnetic radiation may be done using small aerials tuned to the desired transmission/reception frequency. Some frequencies of terahertz radiation can penetrate several millimeters of tissue with low water content, such as fatty tissue, and reflect back. THz radiation can also detect differences in water content and density of a tissue. The THz sensors/transceivers thus allow effective detection of epithelial cancer with an imaging system that is safe, non-invasive, and painless.

Figure 2:
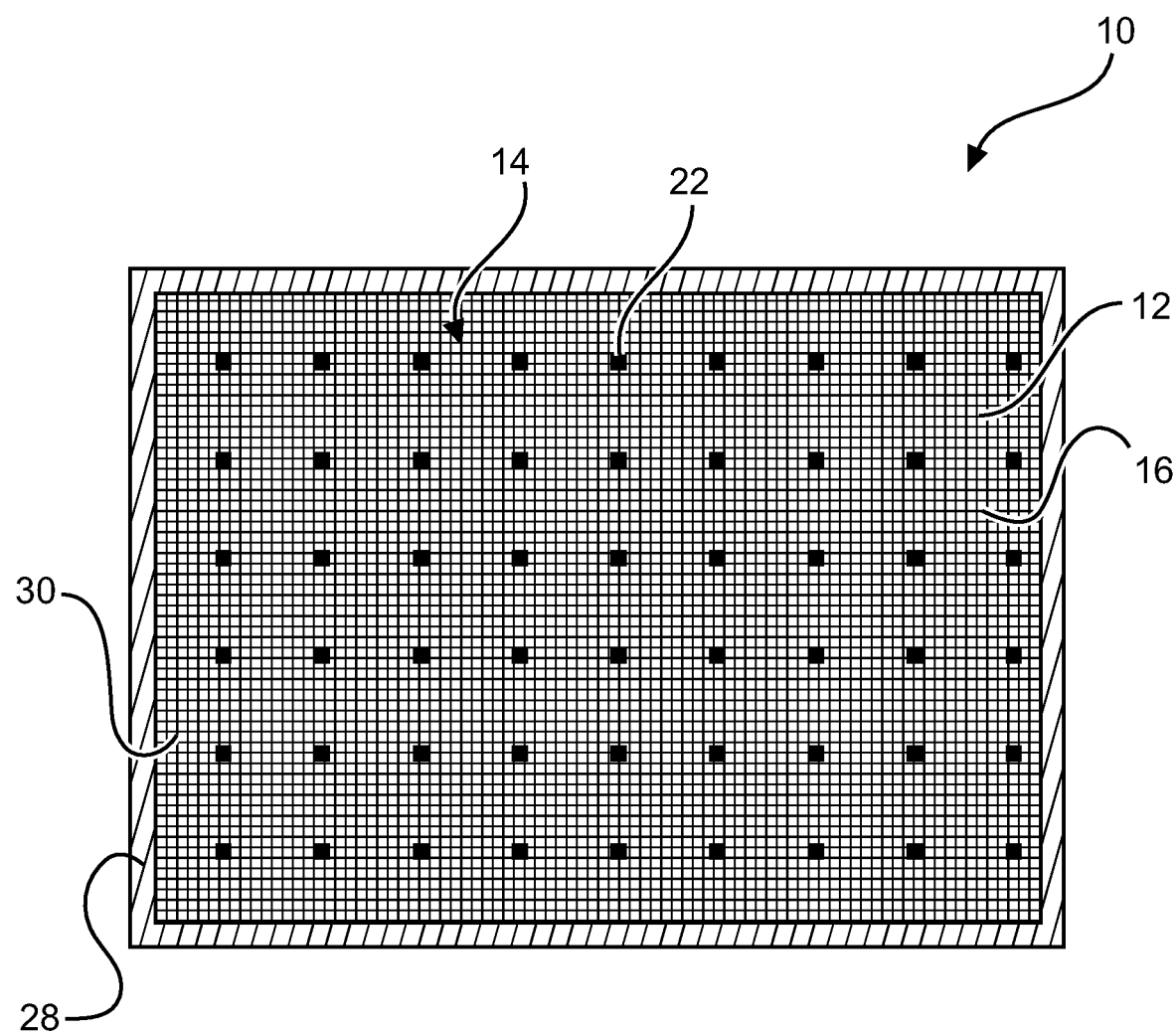
FIG. 2 shows a further exemplary embodiment of a medical imaging detector.

FIG. 2 shows an example, in which the first sensor segment 16 and the second sensor segments 22 are interleaved in a common imaging area 30.

"Interleaving" the first sensors and the second sensors refers to interspersing the second sensors at regular or irregular intervals between first sensors, e.g. by replacing a number of non-neighbouring first sensors or sensor pixels with the second sensors or sensor pixels.

In an example, shown in FIG. 2 as an option, in the first sensor segment 16, a number of non-neighbouring X-ray pixels can be replaced by the second sensor segments 22, e.g. CMUT segments. In the resulting X-ray image, the missing pixels will be replaced by values interpolated from neighbouring pixels to form a contiguous X-ray image. The CMUT segments, i.e. the second sensor segments 22, form an array of similar size as the X-ray sensor, enabling detailed ultrasound images.

Figure 3:
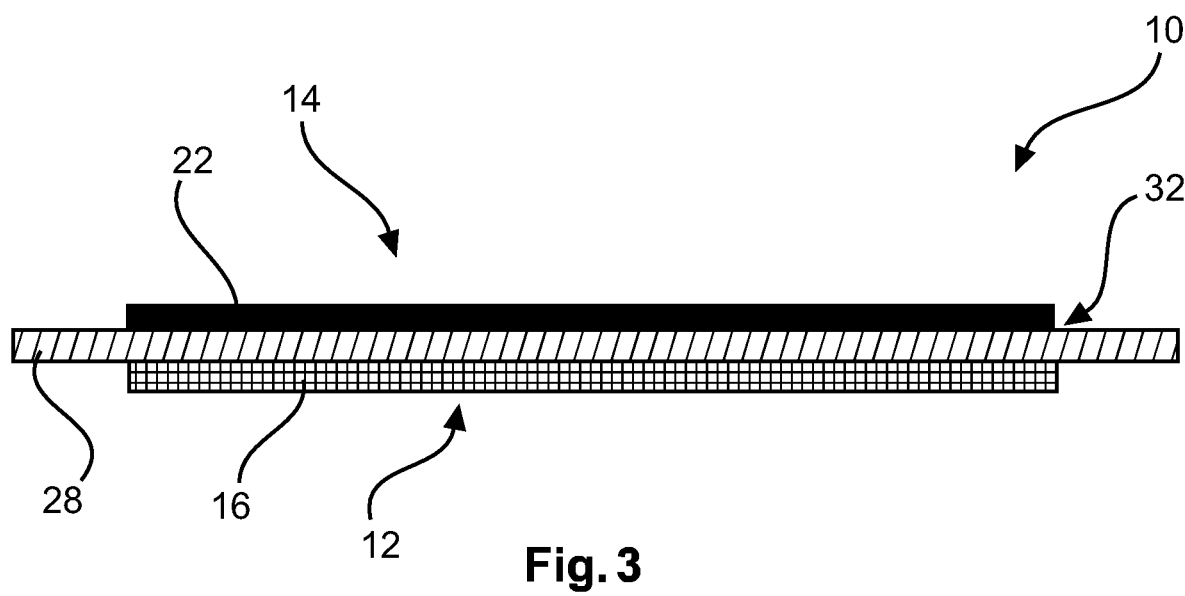
FIG. 3 shows a still further exemplary embodiment of a medical imaging detector.

FIG. 3 shows a further example, in which in a dual-imaging area 32, at least a part of the first sensor segments 16 and the second sensor segments 22 are arranged overlapping to provide dual imaging information for a common imaging area.

In an example, shown in FIG. 3 as an option, the first sensor arrangement 12 and the second sensor arrangement 14 are arranged on opposite sides of the at least one substrate structure 28.

For example, X-ray detector segments, i.e. the first sensor segments 16, are provided on the lower side of the substrate structure 28, and segments 22 of a second (non X-ray) imaging modality, for example ultrasound transducers, are provided on the upper side of the substrate structure 28. The term "lower" refers to a side of the substrate facing away from the object, and also the X-ray source. The term "upper" refers to a side facing towards the object. Hence, the X-ray radiation first passes the upper side before reaching the X-ray detector layer.

By providing e.g. ultrasound transducers on the upper side of the substrate structure 28, the ultrasound transducers are in good acoustical coupling with the object, e.g. a portion of a patient.

Further, it is noted that the transparency of the substrate and the first and second sensor arrangements to a particular wavelength or a particular type of radiation must be considered for this arrangement. For example, if the X-ray sensor is arranged underneath the substrate facing away from the X-ray source, it should be ensured that the sensor arrangement in front of the sensor as well as the substrate does not absorb a significant fraction of the X-rays.

In another example, not further shown, the first sensor segments, i.e. X-ray detector segments, and the second sensor segments, such as optical and IR sensors, are manufactured on separate substrates, e.g. plastic foils, and attached to each other, e.g. by lamination of foils, to from a dual-imaging area. Similarly, the transparency of the sensors and the substrate to a particular wavelength or a particular type of radiation must be considered. For example, thin foils with integrated optical sensors can be placed in front of the X-ray sensors, since they do not absorb a significant fraction of X-rays. On the other hand, infrared sensors can be placed below X-ray sensors, i.e. facing away from the object, since most semiconductors are transparent in the infrared region.

In the above-mentioned examples, the substrate structure is a single layer of a one-piece substrate material. In another example, the substrate structure can comprise two or more sub-layers of material stacked on top of each other to form one substrate layer.

Figure 4:
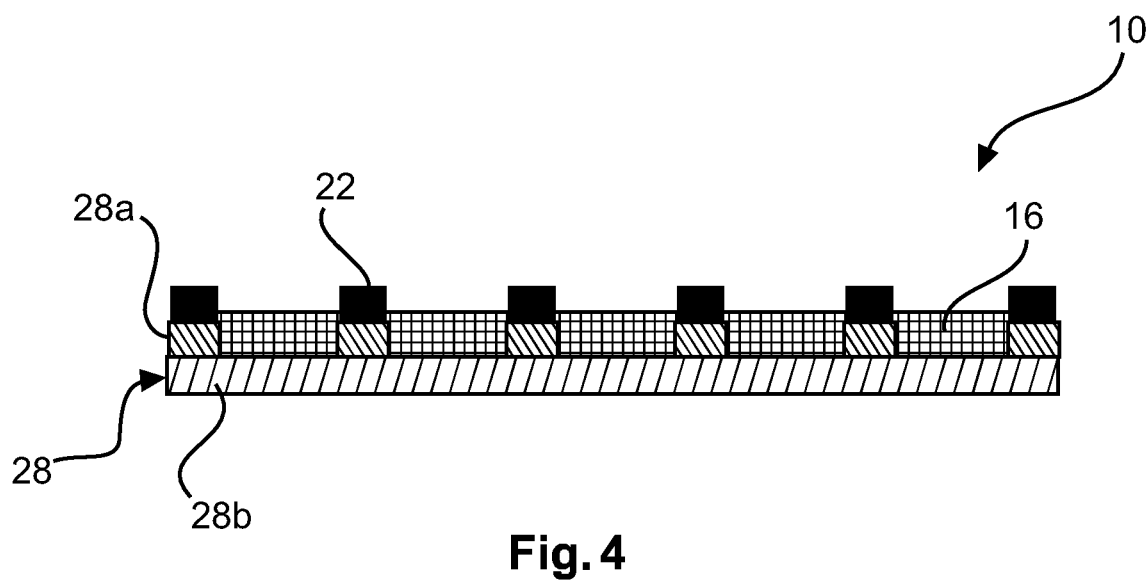
FIG. 4 shows a further exemplary embodiment of a medical imaging detector.

FIG. 4 shows an example, in which the substrate structure 28 comprises two sub-layers of material, i.e. a plurality of intermediate substrates 28a and a base substrate 28b. The first sensor segment 16, i.e. the large area X-ray sensor, may be fabricated on the base substrate 28b, e.g. a silicon substrate. On the other hand, the second sensor segments 22, such as hyper-spectra cameras, may be made using organic semiconductors on plastic foil substrates, i.e. on the intermediate substrates 28a. Some pixels of the first sensor segment 16 are replaced by the second sensor segments 22 by attaching the intermediate substrates 28a to the base substrate 28b.

As a further option, a third sensor arrangement (not further shown) may be provided in the above-mentioned examples. The third sensor arrangement comprises one or a plurality of third sensor segments arranged on the at least one substrate structure. The third segment(s) is (are) a non-imaging sensor(s) comprising at least one of the group of: a telemetry transceiver, a body area network transceiver, an electric field sensor, a magnetic field sensor, an attitude sensor, an acceleration sensor, a motion sensor, and a rotation sensor.

The third sensor segments may be arranged on the substrate according to one of the above-mentioned examples. For example, the third sensor segments may be arranged on the outer periphery of the first imaging area. In another example, the third sensor segments and the first sensor segments are interleaved.

The third sensor arrangement is provided for adding extra information to the image data acquired by the first and second sensor arrangements, like temperature or electric heart signals. In addition, the third sensor arrangement may also be used to enhance the X-ray image acquisition process, e.g. by sensing patient movements, or by measuring patient thickness.

A telemetry transceiver can be used to receive telemetry from other sensors, such as e-pills, distributed in or on the medium to be test, e.g. a patient.

A body area network transceiver allows collecting patient-monitoring data, e.g. blood pressure, body temperature, or heart rate, via a wireless network of sensors arranged on the medical imaging detector.

An electric field sensor, such as a capacitive electric field sensor, may be used for monitoring electrocardiogram (ECG).

A magnetic field sensor may be used to align the medical imaging detector and the X-ray source, e.g. X-ray tube, if the X-ray tube is also provided as a corresponding magnetic field generating coil. A magnetic field sensor may also be provided for sensing the position of an interventional device, such as a catheter head, inside a patient.

Further, an acceleration sensor, a rotation sensor, an attitude sensor, and a motion sensor based on e.g. capacitance, impedance, or pressure measurement, can be used to detect the movements of the medical imaging detector.

A motion sensor may also be provided as an optical sensor or an ultrasound sensor for detecting the relative distance between the patient and the medical imaging detector.

In addition, in order to avoid motion artifacts and the disruption of the signals of interest, additional ultrasound transceivers or optical/IR cameras may be provided for monitoring the posture of a patient during measurements.

Figure 5:
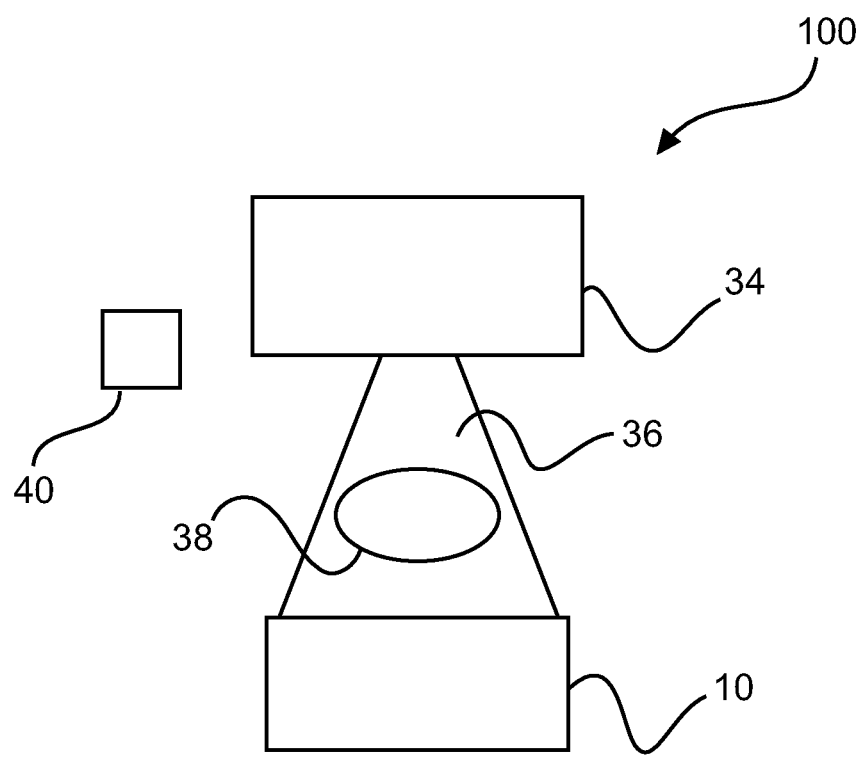
FIG. 5 shows an schematic setup of a medical imaging system according to an exemplary embodiment.

FIG. 5 shows an example of a medical imaging system 100 in a schematic view. The medical imaging system 100 comprises a first imaging source 34 and the medical imaging detector 10 according to one of the above-mentioned examples. The first imaging source 34 is an X-ray source configured to provide X-ray radiation 36 as a first type of radiation to be detected by the first sensor arrangement 12 (not further shown) of the medical imaging detector 10.

An object 38, e.g. a portion of a patient, is irradiated with the X-ray radiation 36 under examination. Parts of the energy of the X-ray beam are absorbed when passing the object 38. On the opposite side of the object 38, the medical imaging detector 10 captures the attenuated radiation, resulting in a medical or clinical image.

The second type of radiation to be detected by the second sensor arrangement of the medical imaging detector may be provided without any additional imaging sources.

For example, the second sensor arrangement comprising at least one visible light sensor is provided on the medical imaging detector. The visible light sensor may be a CMOS image sensor, which is used to detect the contour of an object, e.g. a patient, under an ambient lighting condition, i.e. without using any light sources.

For example, the second imaging source may be light, e.g. visible light, or UV light or IR light existing, or being present, in the surrounding, e.g. the operational theatre, or treatment or examination room. In other words, the second type of radiation can be provided by a second imaging source or by surrounding or environment sources.

According to an example, shown in FIG. 5 as an option, the medical system 100 further comprises a second imaging source 40. The second imaging source 40 is configured to provide a signal to be detected by the second sensor arrangement 14 (not further shown) of the medical imaging detector 10. The second imaging source 40 is provided as at least one of the group of: a light source, an acoustic source, and a radiation source.

It is noted that the position or arrangement of the second imaging source 40 in FIG. 5 is merely for illustration purposes. It will be appreciated that certain types of imaging sources may be integrated in the medical imaging detector 10. For example, an ultrasonic transducer on the medical imaging detector can be used for both sound generation and reception.

Further, as an option, the medical imaging detector 10 is provided with the third sensor arrangement, which is not further shown. The third sensor arrangement is provide for delivering information that is not obtainable from the image data acquired by the first and second sensor arrangements, thus adding clinically relevant information to the primary X-ray images, e.g. temperature, electric heart signals, etc.

Figure 6:
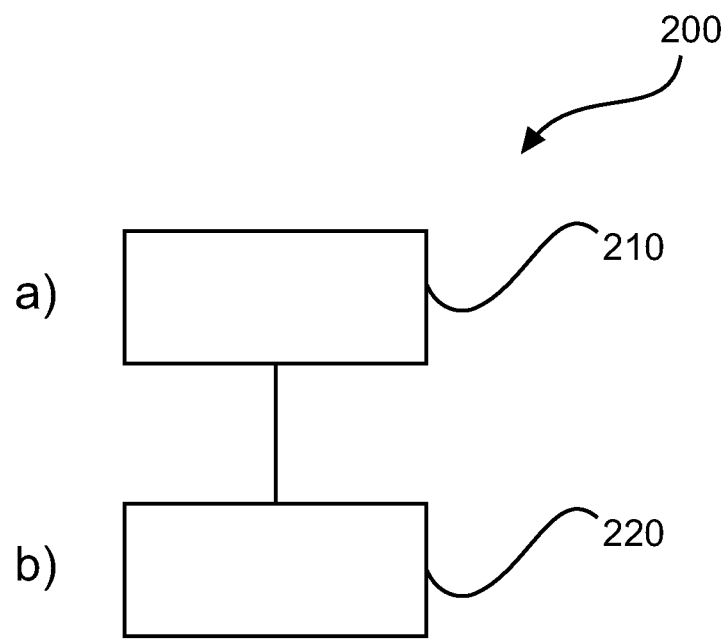
FIG. 6 shows basic steps of an exemplary method for medical imaging examination.

FIG. 6 shows a medical imaging method 200, comprising the following steps: In a first step 210, a first imaging modality examination and a second imaging modality examination are performed on an object. In a second step 220, the first image data of the first imaging modality and the second image data of the second imaging modality are obtained with a medical imaging detector. The first imaging modality is an X-ray imaging modality, while the second imaging modality is a non-X-ray imaging modality. The first image data is acquired in a first imaging area and the second image data is acquired in a second imaging area. The first imaging area and the second imaging area at least partly overlap.

The first step 210 is also referred to as step a), and the second step 220 as step b).

It is to be appreciated that further (sub-) steps may be provided, like aligning and matching the two image data set to overlay two image data sets belonging to two imaging modalities on a single display.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical imaging detector, comprising:
   a first sensor arrangement configured to provide a first type of image data belonging to an X-ray imaging modality, wherein the first sensor arrangement comprises at least one first sensor segment arranged within a first circumferential line defining a first imaging area;
   a second sensor arrangement configured to provide a second type of image data belonging to a non-X-ray imaging modality, wherein the second sensor arrangement comprises at least one second sensor segment arranged within a second circumferential line defining a second imaging area, wherein the second sensor arrangement is located on the outer periphery of the first imaging area, and wherein the first imaging area and the second imaging area at least partially overlap; and
   a substrate structure, wherein the at least one first sensor segment and the at least one second sensor segment are integrated on the substrate structure to enable a substantially simultaneous acquisition of the first and second types of image data.

2. The detector according to claim 1, wherein the at least one second sensor segment is at least one of:
a visible light sensor;
an ultraviolet light sensor;
an infrared light sensor; and
a hyper-spectral sensor.

3. The detector according to claim 1, wherein the at least one second sensor segment is at least one of:
an audible sound sensor;
an ultrasound sensor; and
an infrasound sensor.

4. The detector according to claim 1, wherein the at least one second sensor segment is at least one of:
a terahertz radiation sensor; and
a gigahertz radiation sensor.

5. The detector according to claim 1, further comprising:
a third sensor arrangement comprising at least one third sensor segment integrated on the substrate structure, wherein the at least one third sensor segment is at least one of:
a telemetry transceivers;
a body area network transceiver;
an electric field sensor;
a magnetic field sensor;
an attitude sensor;
an acceleration sensor;
a motion sensor; and
a rotation sensor.

6. The detector according to claim 1, wherein the first sensor segments and the second sensor segments are interleaved in the first and second imaging areas.

7. The detector according to claim 1, wherein at least a part of the first sensor segments and the second sensor segments overlap to provide dual imaging information for the first and second imaging areas.

8. The detector according to claim 1, wherein the first sensor arrangement and the second sensor arrangement are located on opposite sides of the substrate structure.

9. A medical imaging system, comprising:
a medical imaging detector comprising:
a first sensor arrangement configured to provide a first type of image data belonging to an X-ray imaging modality, wherein the first sensor arrangement comprises at least one first sensor segment arranged within a first circumferential line defining a first imaging area;
a second sensor arrangement configured to provide a second type of image data belonging to a non-X-ray imaging modality, wherein the second sensor arrangement comprises at least one second sensor segment arranged within a second circumferential line defining a second imaging area, wherein the second sensor arrangement is located on the outer periphery of the first imaging area, and wherein the first imaging area and the second imaging area at least partially overlap; and
a substrate structure, wherein the at least one first sensor segment and the at least one second sensor segment are integrated on the substrate structure to enable a substantially simultaneous acquisition of the first and second types of image data;
an X-ray source configured to provide X-ray radiation as a first type of radiation to be detected by the first sensor arrangement of the medical imaging detector.

10. The system according to claim 9, further comprising:
an imaging source configured to provide a signal to be detected by the second sensor arrangement of the medical imaging detector; and wherein the second imaging source is at least one of:
a light source;
an acoustic source; and
a radiation source.

11. A medical imaging method, comprising:
performing an X-ray imaging modality examination using a first sensor arrangement that comprises at least one first sensor segment arranged within a first circumferential line defining a first imaging area;
performing a non-X-ray imaging modality examination using a second sensor arrangement that comprises at least one second sensor segment arranged within a second circumferential line defining a second imaging area, wherein the second sensor arrangement is located on the outer periphery of the first imaging area, wherein the first imaging area and the second imaging area at least partially overlap, and wherein the at least one first sensor segment and the at least one second sensor segment are integrated on a substrate structure to enable a substantially simultaneous acquisition of the first and second types of image data.

12. A non-transitory computer readable medium having one or more executable instructions stored thereon, which when executed by a processor, cause the processor to perform a medical imaging method comprising:
performing an X-ray imaging modality examination using a first sensor arrangement that comprises at least one first sensor segment arranged within a first circumferential line defining a first imaging area;
performing a non-X-ray imaging modality examination using a second sensor arrangement that comprises at least one second sensor segment arranged within a second circumferential line defining a second imaging area, wherein the second sensor arrangement is located on the outer periphery of the first imaging area, wherein the first imaging area and the second imaging area at least partially overlap, and wherein the at least one first sensor segment and the at least one second sensor segment are integrated on a substrate structure to enable a substantially simultaneous acquisition of the first and second types of image data.

* * * * *